United States Patent [19]

Smith

[11] Patent Number: 5,666,970

[45] Date of Patent: Sep. 16, 1997

[54] LOCKING MECHANISM FOR CATHETERS

[75] Inventor: Iain S. R. Smith, Boulder, Colo.

[73] Assignee: Heart Rhythm Technologies, Inc., Temecula, Calif.

[21] Appl. No.: 433,228

[22] Filed: May 2, 1995

[51] Int. Cl.⁶ ..................................................... A61B 5/00
[52] U.S. Cl. ............................ 128/772; 607/122; 604/95
[58] Field of Search ............................ 604/95, 264, 280; 607/115–116, 119, 122–123, 126, 96; 128/642, 772; 606/45, 46, 47, 48, 49; 600/146–152

[56] References Cited

U.S. PATENT DOCUMENTS

| Re. 34,502 | 1/1994 | Webster, Jr. | 607/125 |
|---|---|---|---|
| 3,452,740 | 7/1969 | Muller | 128/2 |
| 3,470,876 | 10/1969 | Barchilon | 128/348 |
| 3,521,620 | 7/1970 | Cook | 128/2.05 |
| 3,552,384 | 1/1971 | Pierie et al. | 128/2.05 |
| 3,557,780 | 1/1971 | Sato . | |
| 3,605,725 | 9/1971 | Bentov | 128/2.05 R |
| 3,610,231 | 10/1971 | Takahashi et al. | 128/6 |
| 4,207,873 | 6/1980 | Kruy | 128/6 |
| 4,483,326 | 11/1984 | Yamaka et al. | 128/4 |
| 4,503,842 | 3/1985 | Takayama | 128/4 |
| 4,898,577 | 2/1990 | Badger et al. | 604/53 |
| 5,030,204 | 7/1991 | Badger et al. | 604/95 |
| 5,125,896 | 6/1992 | Hojeibane | |
| 5,170,787 | 12/1992 | Lindegren | 128/642 |
| 5,181,514 | 1/1993 | Solomon et al. | 128/660.09 |
| 5,185,004 | 2/1993 | Lashinski | 604/95 |
| 5,190,050 | 3/1993 | Nitzsche | 128/772 |
| 5,195,968 | 3/1993 | Lundquist et al. | 604/95 |
| 5,228,441 | 7/1993 | Lundquist | 128/642 |
| 5,242,430 | 9/1993 | Arenas et al. | 604/280 |
| 5,242,441 | 9/1993 | Avitall | 606/41 |
| 5,254,088 | 10/1993 | Lundquist et al. | 604/95 |
| 5,255,668 | 10/1993 | Umeda | 128/4 |
| 5,255,684 | 10/1993 | Rello | 128/662.06 |
| 5,257,451 | 11/1993 | Edwards et al. | 29/825 |
| 5,263,493 | 11/1993 | Avitall | 607/122 |
| 5,273,535 | 12/1993 | Edwards et al. | 604/95 |
| 5,281,217 | 1/1994 | Edwards et al. | 606/41 |
| 5,284,128 | 2/1994 | Hart | 128/4 |
| 5,318,525 | 6/1994 | West et al. | 604/95 |
| 5,325,845 | 7/1994 | Adair | 604/95 X |
| 5,327,905 | 7/1994 | Avitall | 128/772 |
| 5,330,466 | 7/1994 | Imran | 606/13 |
| 5,346,504 | 9/1994 | Ortiz et al. | 606/192 |
| 5,354,297 | 10/1994 | Avitall | 606/45 |
| 5,358,479 | 10/1994 | Wilson | 604/95 |
| 5,363,861 | 11/1994 | Edwards et al. | 128/772 |
| 5,364,352 | 11/1994 | Cimino et al. | 604/95 |
| 5,368,564 | 11/1994 | Savage | 604/95 |
| 5,370,678 | 12/1994 | Edwards et al. | 607/101 |
| 5,383,852 | 1/1995 | Stevens-Wright | 604/95 |
| 5,383,923 | 1/1995 | Webster, Jr. | 607/125 |
| 5,385,148 | 1/1995 | Lesh et al. | 128/662.06 |
| 5,395,327 | 3/1995 | Lundquist et al. | 604/95 |
| 5,402,793 | 4/1995 | Gruner et al. | 128/660.1 |
| 5,403,297 | 4/1995 | Imran | 604/281 |
| 5,431,168 | 7/1995 | Webster, Jr. | 128/658 |
| 5,441,483 | 8/1995 | Avitall | 604/95 |
| 5,465,716 | 11/1995 | Avitall | 128/642 |
| 5,471,982 | 12/1995 | Edwards et al. | 128/642 |
| 5,476,495 | 12/1995 | Kordis et al. | 607/122 |
| 5,545,200 | 8/1996 | West et al. . | |

*Primary Examiner*—Mark Bockelman
*Attorney, Agent, or Firm*—Fulwider Patton Lee & Utecht, LLP

[57] ABSTRACT

A locking mechanism for a steerable catheter, the catheter comprising a resilient body member having a restoring force that tends to maintain the body member at a predetermined orientation, and a manipulation handle including a control element and a second element movable in relation to one another and adapted for controlling the orientation of the body member. The locking mechanism maintains the selected deflection of the body member against the restoring force but permits a physician to overcome the locking force by moving the control element. The locking mechanism does not interfere with the other control movement of the handle. The locking device has a biasing member and a contact member mounted between the control element and the second element. The biasing member urges the contact member into frictional contact with one of the elements for holding the control element at the selected longitudinal position.

23 Claims, 5 Drawing Sheets

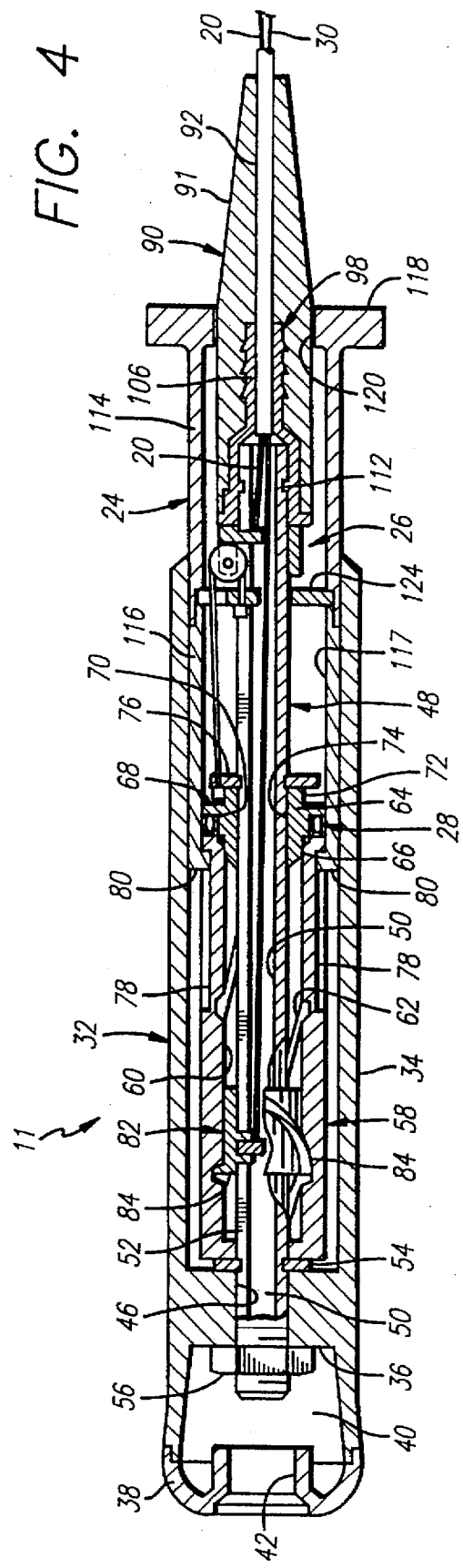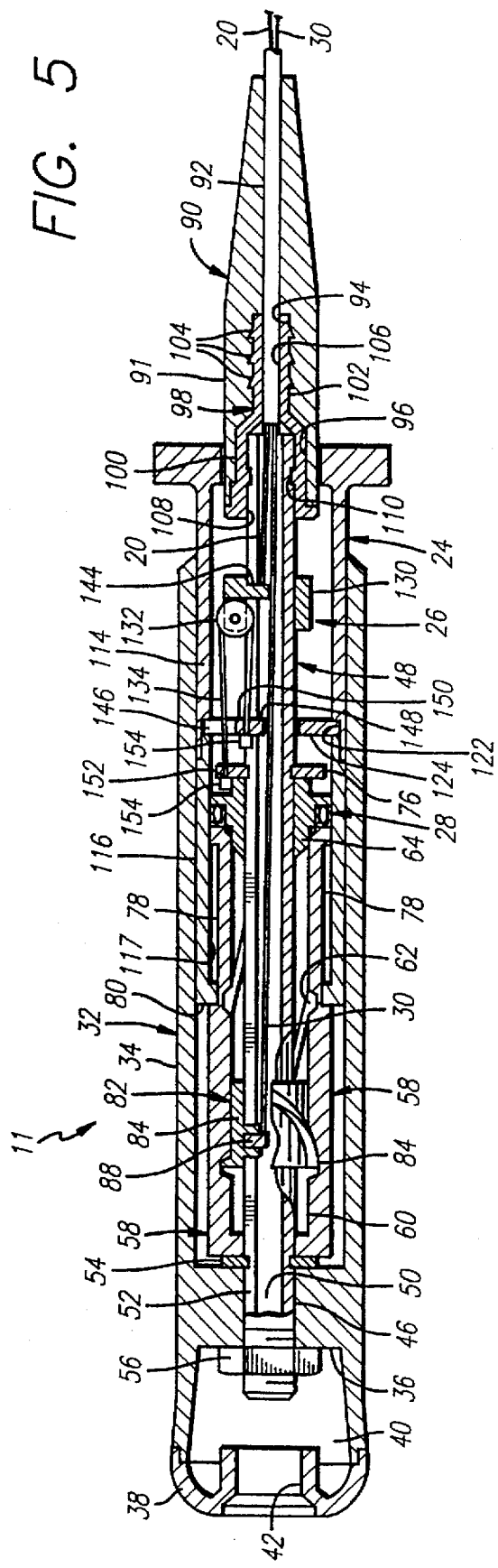

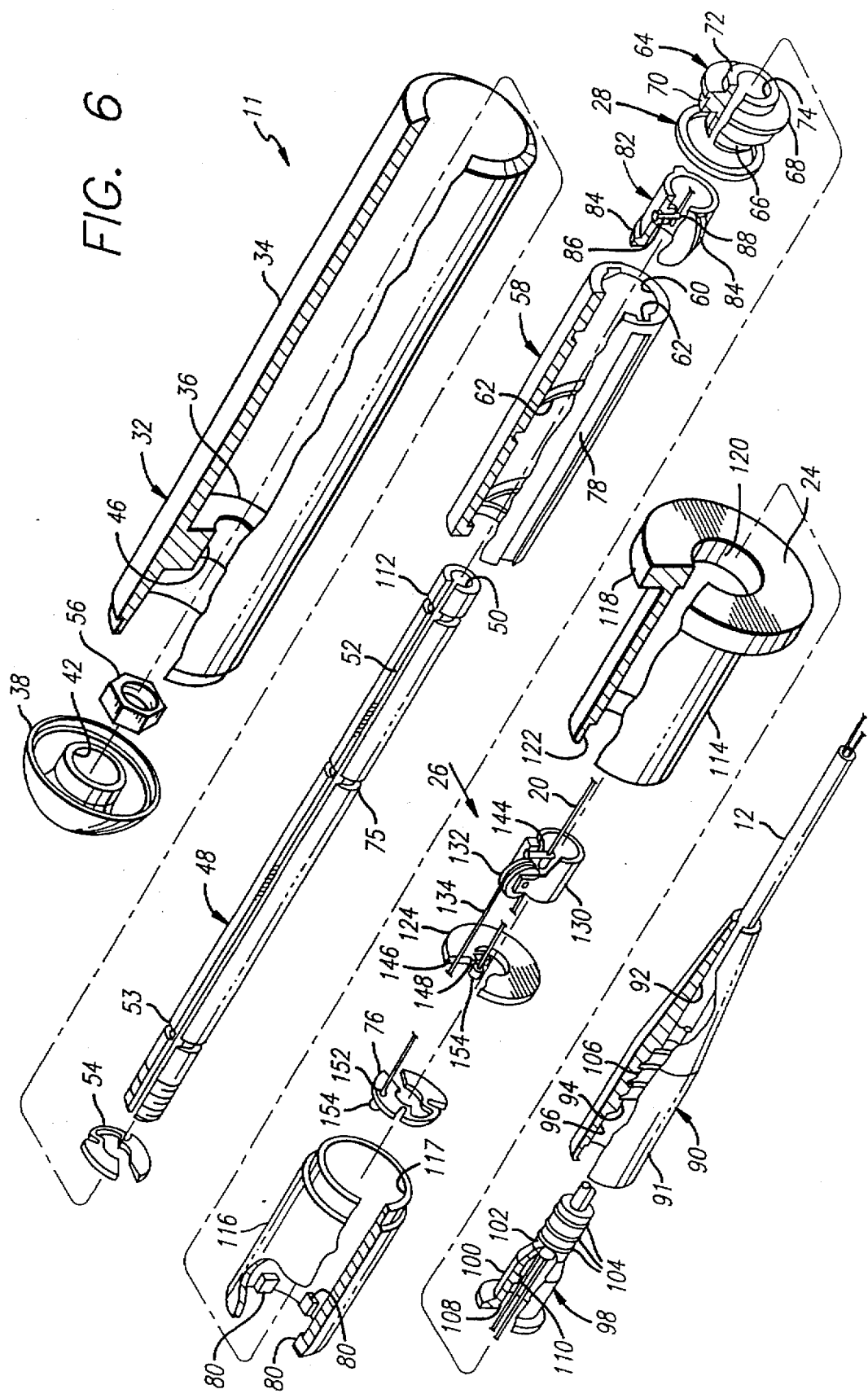

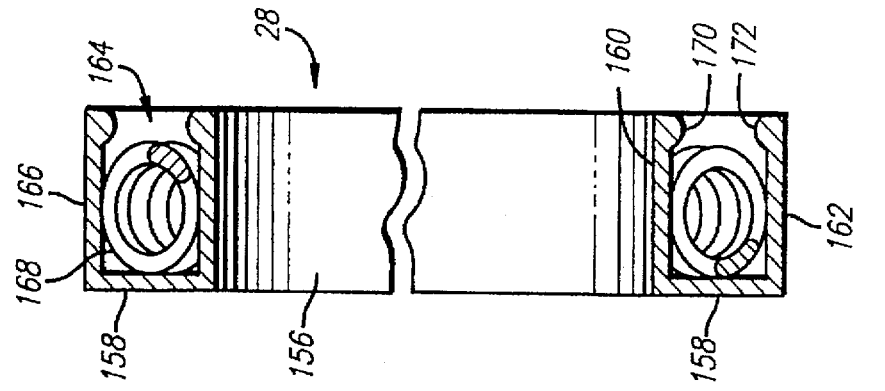
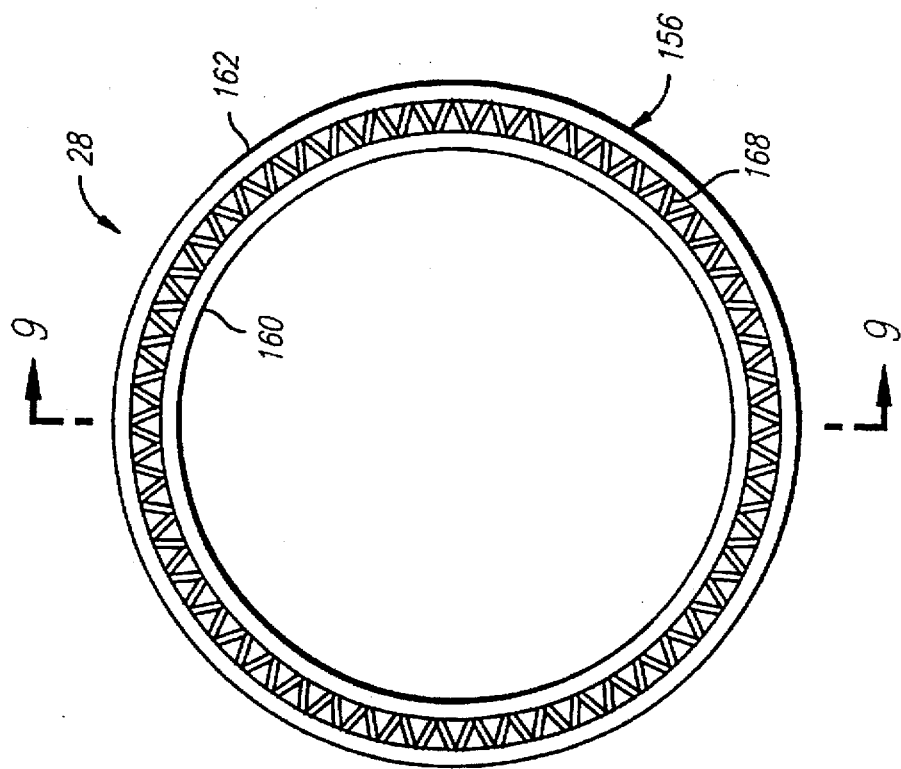
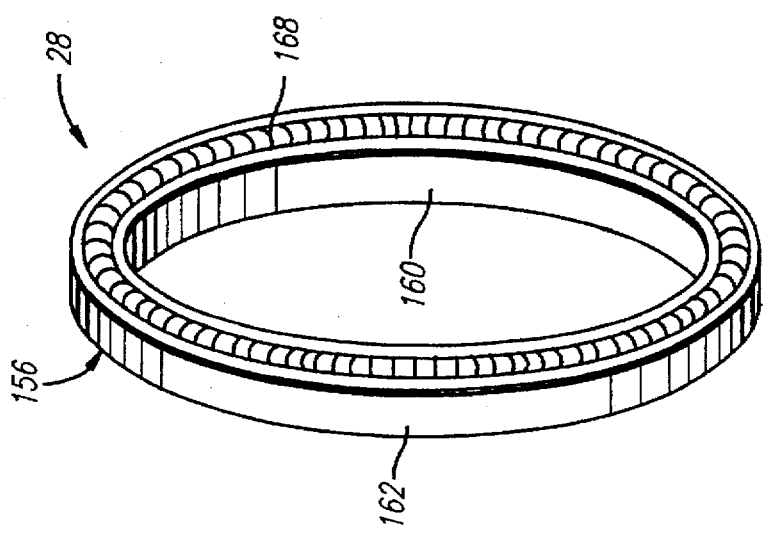

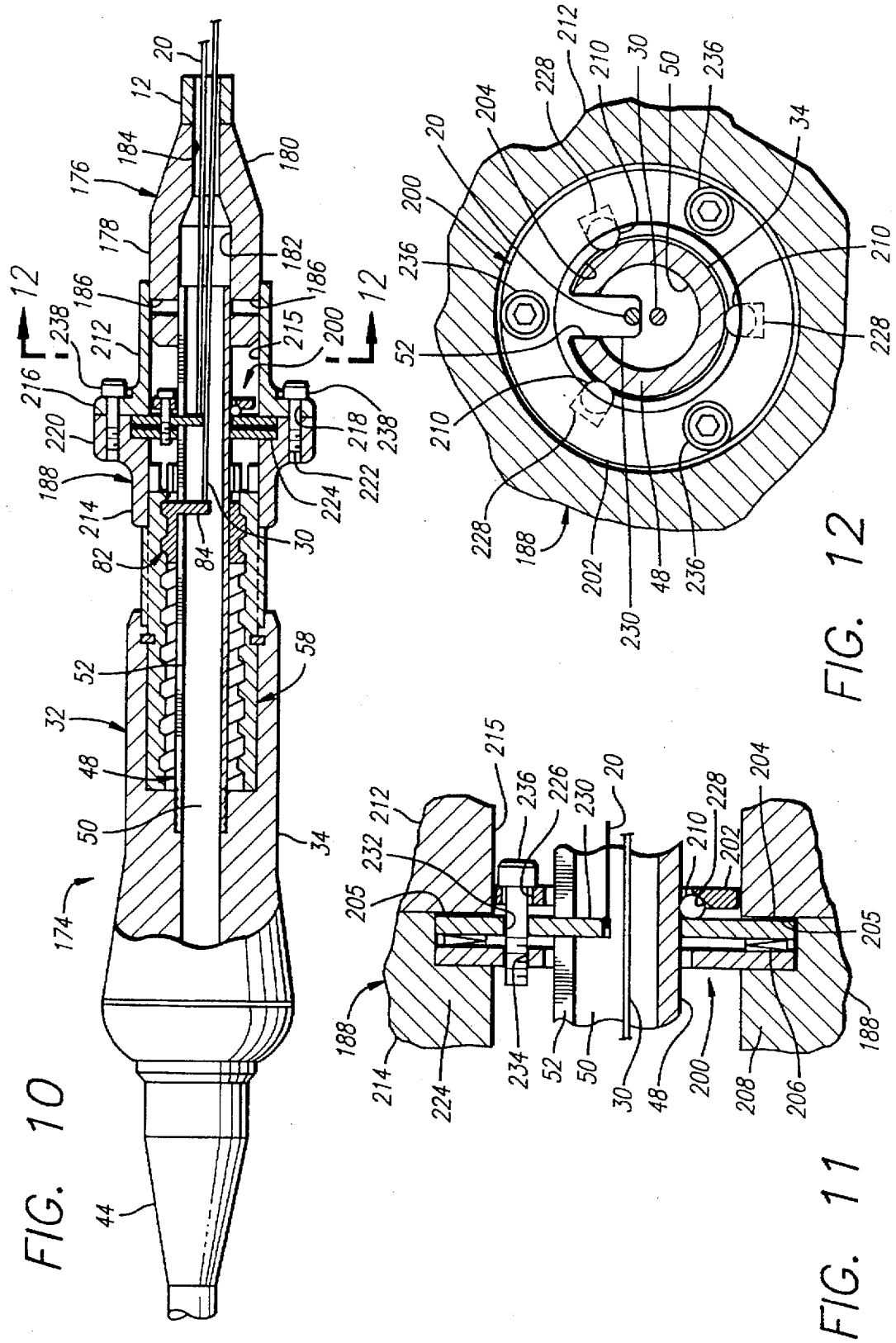

LOCKING MECHANISM FOR CATHETERS

BACKGROUND

The invention relates generally to catheters, and more particularly, to locking mechanisms for steerable catheters.

The heart beat in a healthy human is controlled by the sinoatrial node ("S-A node") located in the wall of the right atrium. The S-A node generates electrical signal potentials that are transmitted through pathways of conductive heart tissue in the atrium to the atrioventricular node ("A-V node") which in turn transmits the electrical signals throughout the ventricle by means of the His and Purkinje conductive tissues. Improper growth of or damage to the conductive tissue in the heart can interfere with the passage of regular electrical signals from the S-A and A-V nodes. Electrical signal irregularities resulting from such interference can disturb the normal rhythm of the heart and cause an abnormal rhythmic condition referred to as cardiac arrhythmia.

Electrophysiological ablation is a procedure often successful in terminating cardiac arrhythmia. This procedure involves applying sufficient energy to the interfering tissue to ablate that tissue thus removing the irregular signal pathway. However, before an ablation procedure can be carried out, the interfering tissue must first be located.

One location technique involves an electrophysiological mapping procedure whereby the electrical signals emanating from the conductive endocardial tissues are systematically monitored and a map is created of those signals. By analyzing that map, the interfering electrical pathway can be identified. A conventional method for mapping the electrical signals from conductive heart tissue is to percutaneously introduce an electrophysiology ("EP") catheter having mapping electrodes mounted on its distal extremity. The catheter is maneuvered to place those electrodes in contact with or in close proximity to the endocardium of the patient's heart. By monitoring these signals, aberrant conductive tissue sites responsible for the arrhythmia can be pinpointed.

Once the origination point for the arrhythmia is located, the physician may use an ablation procedure to restore normal heart beat or at least improve the heart beat. Successful ablation of the conductive tissue at the arrhythmia initiation site usually terminates the arrhythmia or at least moderates the heart rhythm to acceptable levels.

In order to perform the above described electrophysiological procedures, the EP catheter, having mapping and ablation electrodes at the distal end thereof, is percutaneously introduced into the cardiovascular system of the patient through a blood vessel, for instance the femoral artery, and advanced to a selected endocardial site in the atrium or ventricle. Once the EP catheter has reached the heart, it must be maneuvered to place its electrodes or other active devices in the required positions to perform the EP procedures.

A steerable catheter may be used that has an internal deflection control line attached at a point adjacent the distal tip of the catheter. Pulling the proximal end of the control line at the manipulation handle causes the distal tip of the catheter to bend in one direction so that the tip may be directed to a selected endocardial site. The ability to position these devices at the target site is important to obtaining good ablation results.

Most steerable catheters have catheter tubes or shafts formed of an elongated flexible, yet resilient material, so that when the tube is in its relaxed state, it tends to maintain a generally straight configuration. The tension on the control line overcomes the natural resilient straightening forces so that a deflection and a curved configuration results. The natural resilient straightening forces of the catheter tube oppose deflection forces applied by the physician to the control wire. If those straightening forces are strong enough, the physician may need to continuously apply pressure to the control wire to maintain a deflection of the distal end. Requiring the physician to apply continuous and substantial force to hold a distal end deflection can cause tiring as well as decreased accuracy in maintaining a certain deflection.

In order to free the physician's hand from having to continuously apply force, it is therefore desirable for the steerable EP catheter to include a locking mechanism that holds the tip deflection control line at the position selected to maintain the catheter distal end curvature and oppose the resilient straightening force of the catheter tube. Such a feature would be useful for maintaining intimate electrode contact with a particular selected endocardial tissue site during mapping and ablation procedures. The curvature and position of the distal portion of the catheter may have to be finely adjusted one or more times in order to facilitate complete and comprehensive monitoring of the electrical signals emanating from the conductive heart tissue for effective mapping and detection of arrhythmatic points of origin. In addition, in order to foster precise location of the ablation electrode adjacent selected endocardial treatment sites, frequent but minute repositioning of the tip electrode thereof may often be required to facilitate accurate effective ablation of the aberrant heart tissue. Therefore, a deflection control line locking mechanism should provide increased repositioning and locking resolution, allowing for fine catheter distal end curvature control.

One control line locking mechanism utilizes a toothed lever pivoted on a sleeve, the lever selectively engaging ratchet threads disposed on a steerable catheter handle. The catheter handle is connected to the proximal end of a deflection control line so that pulling the handle longitudinally relative to the sleeve deflects the distal end of the catheter and the toothed lever on the sleeve engages the ratcheted threads to hold the control line in position. Although this type of mechanism has been found effective in certain instances, locking resolution and therefore distal end curvature control is restricted to the resolution defined by the ratchet spacing of the handle, which can be rather coarse.

Another deflection control line locking mechanism uses an externally threaded control member attached to the proximal end of the control line. The externally threaded member is threadedly engaged to an internally threaded collar, whereby rotation of the collar relative to the member, pulls the control line and threaded friction therebetween holds the control line at its selected position. Although this locking device allows for increased catheter distal end curvature resolution, many revolutions of rotation may be required to affect the curvature, which in turn can slow down the catheter steering process.

Yet in another control line locking mechanism, O-rings are disposed between the proximal end of the catheter tube and the manipulation handle. The manipulation handle is attached to the proximal end of the control line so that pulling the handle longitudinally relative to the catheter tube deflects the distal end thereof. The O-ring holds the handle relative to the catheter tube so that the control line device is held in the selected position. However, O-rings may "creep" over time and use and not retain the frictional contact between surfaces required to effectively lock those surfaces relative to one another. Furthermore, should bodily fluids, or the like, come into contact with the surface of the O-ring, the O-ring may tend to slip releasing the control line from its locked position. In addition, the O-ring may tend to twist and rip as the control line device is moved relative to the manipulation handle. Moreover, if the O-ring is constructed of an overly elastic material the O-ring may tend to adhere to the manipulation handle and bind or stick the handle and catheter relative to one another.

In one steerable catheter, a stiffening member or mandrel is also located in the catheter tube in addition to the control line, and includes a stiffening member control device mounted to the manipulation handle that may be moved relative to the catheter tube and control line to stiffen the catheter shaft and to alter the radius of bend at the distal end. For instance, a mandrel may be moved towards the distal end or more towards the proximal end of the catheter to alter the radius of bend at the distal end, providing an additional degree of selective steering control.

Where a threaded element is used to advance and retract the mandrel, the frictional properties of the threaded element sufficiently lock the mandrel in its selected position overcoming the natural straightening forces of the catheter tube. It is desirable that the deflection control line locking mechanism not interfere with the independent rotatable operating and locking characteristics of the threaded element controlling the stiffening member.

Hence, those skilled in the art have recognized the need for a steerable catheter having the ability to lock the distal end deflection of the catheter at the selected position. In addition, the deflection control line locking mechanism should provide increased locking resolution allowing for freer catheter distal end curvature control. Furthermore, the deflection control line locking mechanism should not interfere with the operation of other steering control mechanisms and should be relatively easy to operate, inexpensive to manufacture, and reliable in use. The present invention fulfills these needs and others.

SUMMARY OF THE INVENTION

The present invention is directed to a locking mechanism for maintaining a selected shape of a catheter shaft. Briefly and in general terms, the locking device is incorporated in a catheter including a resilient body member having a predetermined shape, and a manipulation handle having first and second elements that are movable in relation to one another to control the shape of the body member. The locking mechanism secures the first and second elements in relation to each other at the selected relative position.

More particularly, the resilient body member has a restoring force that tends to maintain itself at and restore itself to a predetermined shape. Movement of the first and second elements of the handle in relation to each other overcomes that restoring force and changes the shape of the body member. When the first and second elements are released, the locking device also overcomes the restoring force and holds the first and second elements at the selected position to maintain the presently selected shape of the body member.

In one aspect, the locking mechanism is used with a manipulation handle attached to the proximal end of the body member having first and second elements movable in relation to each other and comprises a deflection control device mounted in the body member and connected at a proximal end to the first element of the handle and extending into the distal end of the body member wherein movement of the first element in relation to the second element results in movement of the control device in the distal end, said movement in one direction causing deflection of the distal end from its predetermined shape against the restoring force, said restoring force also tending to cause movement of the first element in relation to the second element. A locking device has a contact member and a biasing member mounted on the first element with the contact member being continuously urged into contact with the second element by the biasing member, said biasing member providing a force against said contact member that exceeds the restoring force provided by the body member so that the locking member holds the first and second elements in a selected position relative to one another and thereby maintains the control device at a selected position in the distal end.

In more detailed aspects, the contact member comprises an annular contact arm having a circumferential contact surface and the biasing member is disposed in contact with the contact arm to urge the arm against the second element and bias the contact surface to exert radial pressure against the second element. The contact member is U-shaped in cross section having inner and outer arms, one of the arms being the contact arm and the volume between the arms defining an annulus in which the biasing member is mounted, the biasing member having a size selected to urge one of the arms outward from the annulus into contact with the second element.

In further detailed aspects, the biasing member comprises an annular coil spring of a size selected so that energy is stored in the spring when mounted in the annulus tending to urge the contact surface into contact with the other element. The coil spring is under radial compression when disposed in the annulus of the contact member, the spring tending to expand and displace the contact arm into contact with the second element pressing the contact surface against the second element.

In yet a further aspect, the second element surrounds the first element and slides in relation to the first element, and the contact member is mounted at a fixed position on the first member and is biased into contact with the second member to secure the second member at a selected position to which it has been slid in relation to the first member.

In other aspects, the second member is mounted at an external position on the manipulation handle so that it is available for slidable movement by the application of external force by a catheter operator. The first element and second element are mounted so as to be movable axially and rotationally relative to one another, and the contact member comprises a lubricous material that contacts the second element and is mounted so that the contact member provides no significant force to oppose the rotation.

In another aspect of the invention, the contact member comprises a ball and the biasing member urges the ball into contact with the second element to hold the first element in position relative to the second element. More particularly, the biasing member provides an axial force against the ball and the locking device further comprises a biasing surface disposed opposite the biasing member from the ball to redirect the axial biasing force applied to the ball in the radial direction to urge the ball against the other element and hold the first element relative to the second element.

More particularly, in this aspect of the invention, the locking device may further include a first ring mounted to one of the surfaces and a second ring mounted a predetermined axial distance from the first ring. The first ring may include the biasing surface at approximately a forty-five degree angle relative to the axial force for redirect the force applied to the ball in the radial direction against the second element.

In a more detailed aspect, the biasing surface may comprise a plurality of tapered slots wherein a respective ball is disposed in each of the respective slots. Here, the biasing member provides the axial force against each of the respective balls and the tapered slots redirect the force applied to the balls in the radial direction against the other element.

More particularly, the biasing member may be an annular metallic wavy washer spring disposed between the first ring and the second rings and is under axial compression to provide the axial biasing force.

Other aspects and advantages of the invention will become apparent from the following detailed description and accompanying drawings, illustrating by way of example the features of the invention.

BRIEF DESCRIPTION OF THE DRAWINGS

FIG. 4 is a side view, partially in section, of a manipulation handle secured to the proximal end of the catheter taken along line 4—4 of FIG. 1 including the locking device in accordance with a first aspect of the invention but without the connector at the proximal end;

FIG. 5 is a side view, partially in section, of the manipulation handle shown in FIG. 4 illustrating the control element of the handle moved in a proximal direction relative to the position shown in FIG. 4;

FIG. 6 is an exploded perspective view, partially in section, of the manipulation handle shown in FIGS. 4 and 5;

FIG. 7 is an enlarged perspective view of the locking device of FIGS. 4 and 5;

FIG. 8 is a plan view of the locking device shown in FIG. 7;

FIG. 9 is a cross sectional side view of the locking device taken along lines 9—9 of FIG. 8;

FIG. 10 is a side view, partially in section, of an alternate locking mechanism mounted in a manipulation handle secured to the proximal end of the catheter;

FIG. 11 is an enlarged, partially sectional side view, of the locking device of FIG. 10; and FIG. 12 is an end view of the locking device taken along line 12—12 of FIG. 10.

DETAILED DESCRIPTION OF THE PREFERRED EMBODIMENTS

Figure 1:
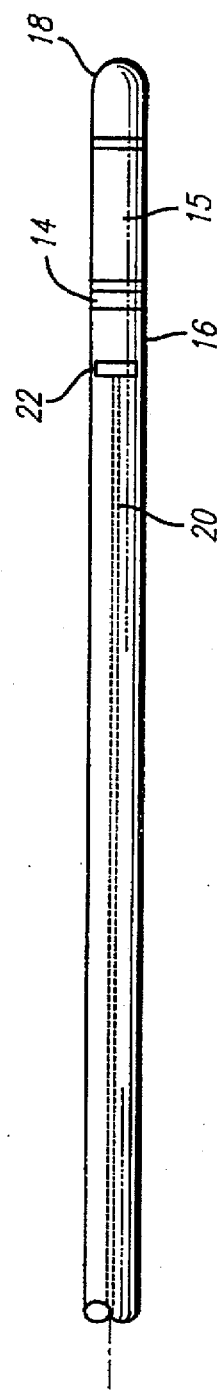
FIG. 1 is a side view of an electrophysiological catheter embodying features of the invention.

In the following description, like reference numerals will be used to designate like or corresponding elements among the several figures of the drawings. Referring now to the drawings and particularly to FIG. 1, there is shown a catheter 10 usable for electrophysiological procedures and embodying features of the invention. Briefly, the catheter 10 includes a manipulation handle 11, an elongated catheter shaft or body member 12, a body member deflection control line 20, and a locking device to hold the body member at deflected positions.

The catheter 10 includes a plurality of sensing electrodes 14 and 18 on the exterior of the body member 12, along the distal end 16 thereof. Also included is an ultrasonic device 15 that may be used for ablation procedures. The body member or shaft 12 has an inner lumen (not shown) that extends to the distal tip and that has disposed therein electrical conductors (not shown) having distal ends electrically connected to the sensing electrodes 14 and 18 and the ultrasonic device 15. Although two sensing electrodes 14 and 18 are shown, more or fewer of these electrodes may be used depending on the application. Additionally, the types of devices mentioned for sensing and ablation are only for purposes of illustration.

Figure 3:
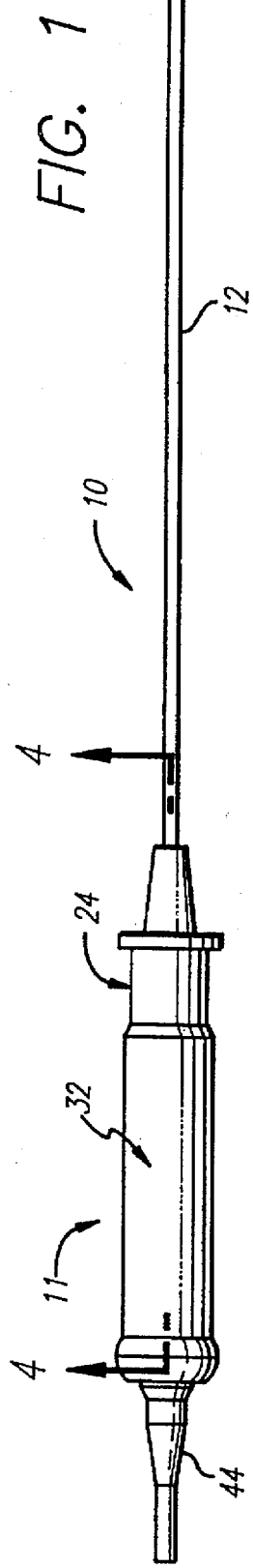
FIG. 3 is a schematic side view of a distal portion of the catheter similar to that shown in FIG. 2, except that in addition to tension being applied to the control line, a stiffening member is advanced into the distal portion of the catheter.
Figure 3:
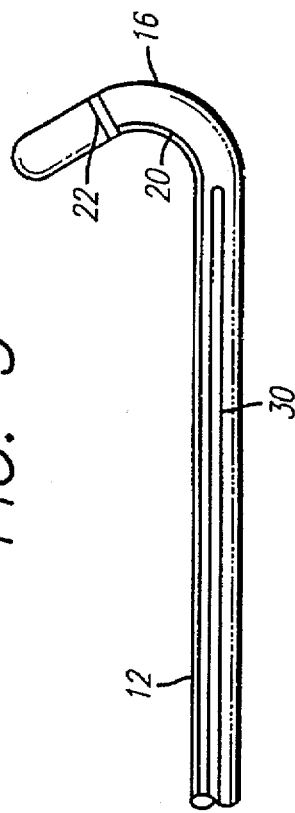
Figure 2:
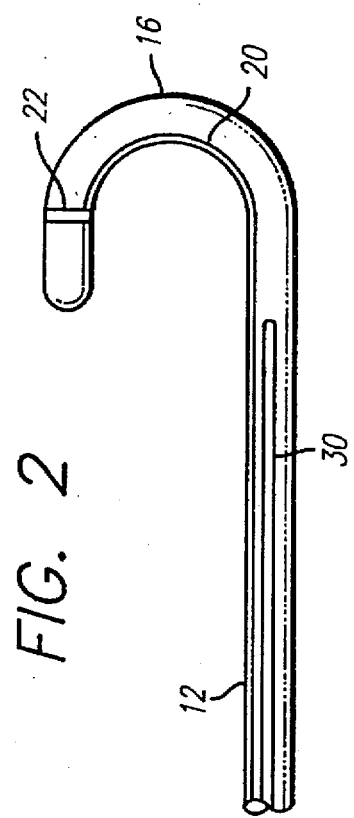
FIG. 2 is a schematic side view of the distal portion of the catheter shown in FIG. 1 with tension applied to a control line to deflect the distal end.

Referring now to FIGS. 1, 2, and 3, the deflection control line 20 is disposed within the catheter body member 12 and has its distal end located at the distal end 16 of the body member 12. The deflection control line 20 has a lubricous coating or jacket (not shown) applied thereover. The body member 12 is fabricated of a flexible resilient material and is constructed in substantially a straight configuration so that when a bending force is applied, the body member supplies an opposing straightening or restoring force that tends to straighten the member 12 to its nondeflected state and return to a straightened position when the bending forces have been removed. A deflection control line 20 is used to impart such bending forces counteracting the body member's 12 restoring force. The distal end of the deflection control line 20 is fixed to an anchor band 22 in the distal end 16 of the catheter body member 12. The distal end of the deflection control line 20 is secured by brazing, soldering or other means to the anchor band 22. Preferably, the control line is disposed within another lumen formed in the catheter body member 12 so as to be off-set from the central longitudinal axis of the catheter body member 12.

When tension is applied to the deflection control line 20 by means of a control element 24 mounted on the manipulation handle 11 at the proximal end of the catheter body member 12, the flexible distal end 16 of the body member will be deflected from its at rest position as shown in FIG. 1 to a curved shape as shown in FIG. 2. In particular, when the control element 24 is pulled longitudinally rearwardly with respect to the manipulation handle 11, a tension force is imparted to the deflection control line 20 to overcome the straightening force of the body member 12 and deflect the distal end of the catheter to a selected curvature.

Once a selected curvature has been attained, the user may desire to free his hand from the control element 24 to perform other tasks. Therefore, a locking device, described below in detail, is provided to counter the restoring force of the catheter body member 12 and hold the control element at the selected position relative to the handle 11 to maintain the selected catheter distal end 16 curvature.

The catheter 10 also includes a mandrel or stiffening member 30 slidably disposed within an inner lumen (not shown) of the body member 12. The advancement of the stiffening member 30 within the distal end 16 of the catheter body member 12 controls the stiffness of the distal end and, in conjunction with the deflection control line 20, controls the shape of the flexible distal end.

The deflection control line 20 and stiffening member 30 are preferably formed of a stainless steel suitable for in vivo use. In one embodiment, the control line 20 is about 0.127 to 0.254 mm (0.005 to 0.010 in.) in diameter and the stiffening member 30 is about 0.254 to 0.508 mm (0.010 to 0.020 in.) in diameter, and the lengths thereof are appropriate for the catheter in which they are utilized.

In FIG. 2, the stiffening member 30 is shown substantially withdrawn from the distal end 16 of the catheter body member 12 so that tension applied to the deflection control line 20 will result in the curvature of the distal end 16 as shown. As depicted in FIG. 3, the stiffening member 30 has been advanced into the distal end 16 of the body member 12, wherein the curvature of the body member is correspondingly altered. Cooperation of the stiffening member and the control line allows for selective variability of the distal end radii of curvature resulting in increased capabilities for distal end intracardial placement.

Referring now to FIGS. 4, 5 and 6, the manipulation handle 11 including the locking device 28 of the preferred embodiment will be described hereinafter in detail. The handle 11 includes a handle body 32 formed with an elongated hollow cylindrical sleeve 34 having a partition wall 36 near the proximal end thereof and a contoured cap 38 affixed to the proximal end of the handle body that encloses a hollow proximal cavity 40. The contoured cap 38 includes an axial connector bore 42 in which a receptacle may be mounted for receiving an external electrical connector 44 (FIG. 1). A suitable receptacle may be obtained from REDEL, a division of LemoUSA, Santa Rosa, Calif. Other suitable electrical receptacles are commercially available.

The partition wall 36 of the handle body 32 is formed with an axial bore 46 therethrough for receipt of a tubular shaft 48 having an inner lumen 50 and a longitudinal slot 52 extending along the length thereof. The shaft, near the proximal end thereof, has a peripheral groove 53 (FIG. 6) for receiving a spring clip 54 and the proximal extremity of the shaft is threaded. The proximal end of the shaft is received within the bore 46 of the partition wall 36 so that the threaded extremity projects rearwardly therefrom. A nut 56 is thereafter threaded onto the proximal end of the shaft to sandwich the partition wall between the spring clip 54 and the nut anchoring the shaft to the handle body concentrically within the hollow sleeve 34 thereof.

The electrical leads of the sensing and ablation conductors (not shown) are located in the inner lumen 50 of the tubular shaft 48, and are electrically connected to the electrical connector receptacle (not shown).

An elongated generally cylindrical nut element 58 surrounds the shaft 48 and has a longitudinal through bore 60. The bore is formed with a pair of opposed helical grooves 62 along its longitudinal length. The distal end of the nut element 58 abuts a generally cylindrical bushing 64. The bushing is mounted on the shaft 48 and is free to rotate in relation to the shaft.

Referring particularly to FIGS. 4 and 6, the bushing 64 is formed with a proximally projecting cylindrical boss 66 sized for receipt within the distal end of the bore 60 of the nut element 58. The bushing 64 has a larger diameter cylindrical flange portion 68 formed with a circumferential locking device groove 70 for receiving the locking device 28 therein. The bushing further includes a smiler diameter distally projecting cylindrical spacer 72, the bushing having an axial bore 74 therethrough sized for receipt of the tubular shaft 48. The bushing is affixed to the distal end of the nut element 58, for instance, using a suitable adhesive.

The nut element 58 and bushing 64 are disposed over the tubular shaft 48 concentrically within the sleeve 34 of the handle body 32 so that the end of the nut element 58 opposite the bushing 64 abuts the spring clip 54 at the proximal end of the handle body 32. The medial portion of the shaft includes a retaining groove 75 (FIG. 6), spaced a predetermined distance from the spring clip 54. The retaining groove 75 is sized for receipt of a nut element locking spring clip 76 abutting the spacer 72 of the bushing 64 to restrain the nut element 58 from longitudinal movement, while allowing rotational freedom thereof. The nut element 58 acts as a nut and is rotatable with respect to the handle body 32.

The nut element 58 is provided with a plurality of longitudinally extending guide tracks 78 on the exterior thereof that are adapted to slidably receive respective longitudinal splines 80 disposed on the interior surface of the control element 24, described in more detail below. As such, confrontation between the splines and tracks during rotation of the control element 24 relative to the handle body 32 causes rotation of the nut element 58 while slidable longitudinal movement of the control element 24 relative to the nut element 58 and handle body 32 is provided.

Referring to FIGS. 4, 5, and 6, a hollow screw element 82 is received within the bore 60 of the nut element 58 and includes a pair of opposed projecting helical ridges or threads 84 sized for complementary threaded engagement within the helical grooves 62 of the nut 58. As shown in FIG. 6, the screw element includes an inward projection 86 having an inwardly projecting metallic pin 88. The screw element is disposed over the shaft 48 and the inward projection 86 is received within the longitudinal slot 52 of the shaft so that rotation of the screw element is constrained, while longitudinal movement relative to the shaft 48 and nut element 58 is provided.

As shown in FIG. 5, the stiffening member 30 is passed proximally through the inner lumen 50 of the shaft 48 and is secured at its proximal end to the pin 88 on the screw element 82 by suitable means such as by brazing, soldering or by an adhesive. The stiffening member 30 is positioned generally at the central longitudinal axis of the shaft 48.

A tapered strain relief 90 is fixedly secured to the distal end of the shaft 48 and includes a generally cylindrical portion 91 tapering therefrom distally to the end of the cap. The distal end of the cap is formed with an axial catheter tube bore 92 stepping proximally to a larger diameter medial bore 94 and tapering therefrom to a further increased diameter proximal bore 96 extending to the proximal extremity of the cap. The medial bore and proximal bore are sized for complementary receipt of a reinforcing sleeve 98.

The reinforcing sleeve 98 has a generally cylindrical portion 100 tapering in the distal direction to a smaller diameter stem 102, the stem having a plurality of annular barbs 104 formed about the periphery thereof. The stem of the reinforcing sleeve has a catheter anchor bore 106 therethrough sized for receipt of the catheter body member 12 and tapers therefrom proximally to a larger diameter shaft bore 108 having a radially inwardly projecting annular ridge 110. The reinforcing sleeve is pressed into the strain relief 90 so that the stem of the sleeve is received in the medial bore 94 and the cylindrical portion of the sleeve is received in the proximal bore 96. The stem barbs 104 engage the periphery of the medial bore to anchor the sleeve to the strain relief. The proximal end of the catheter body member 12 is received in the distal catheter tube bore 92 and anchor bore 106, and affixed therein by suitable adhesive.

The distal end of the tubular shaft 48 includes a circumferential groove 112 (FIGS. 4 and 6) for receipt of the peripheral ridge 110 of the reinforcing sleeve 98. The shaft bore 108 of the reinforcing sleeve 98 is slidably disposed over the distal end of the tubular shaft 48 so that the ridge 110 is disposed in the groove 112. The reinforcing sleeve is secured by a suitable adhesive to the shaft so that the strain relief 90 is affixed to the distal end of the tubular shaft 48.

With continued reference to FIGS. 4, 5 and 6, the control element 24 is described in further detail. The control element is constructed of two pieces and includes a generally tubular distal sleeve element 114 and a tubular proximal sleeve element 116, the proximal sleeve element having an axial bore 117 therethrough. The tubular walls of the respective sleeve elements are of substantially the same radial thickness. The axial bore 117 of the proximal sleeve element is sized for slidable receipt of the nut element 58 therein and the outer diameters of the respective sleeve elements are sized for slidable receipt within the hollow sleeve 34 of the handle body 32. The distal end of the distal sleeve element 114 is formed with a larger diameter knob 118 configured for convenient grasping by the physician and the inner portion of the distal end of the distal sleeve element is formed with a smaller diameter collar 120 for slidable receipt of the cylindrical portion 91 of the strain relief 90. The proximal extremity of the distal sleeve element is formed with an inner annular groove that defines a retention channel 122. The distal end of the proximal sleeve element and the proximal end of the distal sleeve element are joined together to capture the periphery of a control ring 124 within the retention channel 122. When so joined, the sleeve elements form a substantially continuous cylindrical control element 24 that is free to rotate about the control ring 124 without any undue frictional counterforce.

As briefly described above, the control element 24 includes a plurality of inwardly projecting splines 80. In particular, the proximal end of the proximal sleeve element 116 is formed with such splines sized and equiangularly spaced apart for complementary receipt within the guide tracks 78 of the nut element 58. As so constructed, the control element 24 may be rotated within the sleeve 34 of the handle body 32 and the respective splines engage the respective tracks to turn the nut element relative to the handle body 32. The spline and track configuration allows the control element to independently move longitudinally within the sleeve 34 of the handle body, the splines guided within the guide tracks of the nut element.

With continued reference to FIGS. 5 and 6, the catheter deflection control pulley mechanism 26 will now be described. Briefly, the pulley mechanism cooperates with the control element 24 to effectuate control movements of the body member deflection control line 20. The pulley mechanism includes a pulley bracket 130 mounting a pulley 132 that engages a pulley cable 134. The pulley bracket is mounted on the shaft 48 between the ring 124 of the control element 24 and the reinforcing sleeve 98 of the strain relief 90. The pulley bracket includes an inwardly projecting tang 144 disposed distal of the pulley, the proximal end of the distal tip deflection control line 20 secured thereto by soldering, brazing, or other means. The pulley bracket is slidably disposed over the tubular shaft 48 so that the tang 144 and a portion of the pulley are received within the slot 52 of the shaft. As such, the pulley bracket is free to slide longitudinally over the shaft; however, confrontation of the tang and the slot 52 constrains the pulley bracket from rotating relative to the shaft.

The ring 124 of the pulley mechanism 26 includes a radial slot 146 extending from the circumference of the ring inwardly. Inwardly disposed from the slot is a radial inward projection 148 (FIGS. 5 and 6) sized for receipt within the longitudinal slot 52 of the tubular shaft 48, the projection including a small axial bore 150 therethrough. The spring clip 76 is formed with a small bore 152. The respective bores 150 and 152 are sized for receipt of the opposite ends of the pulley cable 134. The pulley cable 134 includes a pair of beads 154 affixed to the opposite ends thereof that are greater in diameter than the pulley cable and bores 150 and 152. One end of the pulley cable is disposed within the spring clip bore 152. The pulley cable is received within the slot 146 of the ring 124 and wrapped around the pulley 132. The other end of the pulley cable is received within the bore 150 of the control ring 124. In this configuration, the pulley bracket, ring 124, and spring clip 76 are constrained from rotational movement relative to the shaft 48 so that the pulley cable 134 does not twist. The pulley cable is maintained in a taut state as tension from the deflection control line 20 pulls on the pulley bracket 130, urging the pulley in a distal direction. For further details, see the copending patent application entitled Catheter Control System Having A Pulley by Thornton et al. filed this same day and having a docket number of 36203.

With particular reference to FIGS. 7, 8, and 9, an embodiment of the locking device 28 is now described in detail. As shown in FIG. 4, the locking device 28 is disposed within the locking device groove 70 of the bushing 64 between the distal extremity of the nut element 58 and the flange portion 68 of the bushing. The locking device includes a contact member 156 which is generally U-shaped in cross section, having a wall 158 formed with inner and outer arms 160 and 162, respectively, the open volume between the arms defining an annulus 164. The outer circumferential portion of the outer arm 162 defines a contact surface 166. Disposed within the annulus is a biasing member, in this case a resilient annular coil spring 168. The spring in its relaxed state has an outside diameter greater that the outer diameter of the annulus thereby providing a biasing force against the outer arm 162. As shown in FIG. 9, the forward end of the inner arm 160 has an annular lip 170, and the forward end of the outer arm 162 also has an annular lip 172; the lips 170 and 172 opposing each other across the annulus 164. The annular lips 170 and 172 engage a peripheral portion of the spring 168 to hold the spring within the annulus 164 and between the arms 160 and 162. The size and shape of the contact member 156 and the spring 168 are selected so that the radially outward biasing force provided by the spring causes the outer arm 162 to expand radially outwardly. The annular spring 168 may be in the form of a metallic, slanted, helical coil spring composed of material, such as stainless steel, that is suitable for hospital use. In alternate embodiments, the biasing means may also take the forms of a U-shaped type leaf spring having slots formed about its periphery to allow bending, a cantilever beam spring, a helical ribbon spring, and others, provided that the spring can develop enough force to lock the movable elements together.

When unassembled, the outer diameter of the contact member 156 of the locking device 28 is slightly smaller in diameter than cylindrical bore 117 of the control element 24. When the manipulation handle 11 is assembled, the bushing 64 having the locking device 28 disposed within the circumferential groove 70 is received within the control element bore 117. When so assembled, the outer arm 162 and the spring 168 of the locking device 28 are compressed radially inwardly. In this compressed state, the spring 168 opposes the inward compressive force and exerts an opposing outward radial force to uniformly press the contact surface 166 of the outer arm 162 against the control element bore 117 imparting a continuous contact force thereto.

Referring again to FIGS. 4 through 6, the operation of the locking mechanism 28 is described in detail. Longitudinal sliding movement of the control element 24 in the proximal axial direction relative to the handle body 32 moves the control ring 124 longitudinally in the proximal axial direction. Because one end of the pulley wire 134 is secured to the control ring 124 and the pulley wire is disposed over the pulley 132, the pulley element 130 also moves in a proximal axial direction but at a one half the displacement of the ring 124. Because the proximal end of the deflection line 20 is secured to the tang 144 of the pulley element, tension is applied to the control line thereby deflecting the distal end 16 of the catheter body member 12. The pulley mechanism increases the mechanical advantage of the force imparted to the control element so that the body member 12 may be deflected more easily. Because movement is at a one-half rate, improved resolution in deflection of the distal end results. Longitudinal movement in the distal direction lessens the tension applied to the deflection control line 20 tending to allow the distal end 16 of the catheter body member to return to its normal straightened shape and reduces the degree of deflection. The physician may selectively position and reposition the control element longitudinally to achieve a selected distal end deflection.

The spring 168 of the locking device 28 is selected to provide a radially outward biasing force that imparts a contact force between the outer arm 162 and the control element bore 117 that is greater than the longitudinal force applied to the locking device by the control line 20 during deflection of the distal end 16 of the catheter body member 12. This contact force therefore locks the control element 24 at the selected position in relation to the handle body 32. The selection of the spring and contact member 156 permits the locking device 28 to overcome the longitudinal force applied to it by the control wire incurred when the control element 24 is moved to any selected position over the entire longitudinal range of motion thereof. The locking device 28 is also designed such that the force it exerts against the control element bore can be overcome without undue effort by the physician who desires to slide the control element 24 relative to the handle body to various selected positions. Additionally, the locking device is designed to reduce the effects of stiction, as described below.

The contact member 156 of the locking device 28, in one embodiment was formed of molybdenum-filled PTFE sold under the trademark of Turcon by American VariSeal, Broomfield, Colo. which is somewhat lubricous to permit longitudinal sliding movement when desired by the physician and yet has sufficient frictional characteristics to hold the control element 24 in a selected position. It is believed that materials of construction for the contact member may include other materials which provide adequate frictional properties yet are non-adhesive in nature.

By using PTFE, which has a lower coefficient of static friction, the problem of stiction is reduced. That is, the operator can slide the control element 24 smoothly from a rest position without the level of stiction that would otherwise cause it to initially stick and then jump free resulting in a jerky motion. However, PTFE is not as resilient as other materials and can take a "set" if left for a period with a force against it. Therefore, the "energized" friction locking mechanism 28 shown in FIGS. 7, 8, and 9 is used in which the biasing means 168 opposes an external inward force on the outer arm 162 that would otherwise cause it to set at an inoperative position. The biasing means continuously urges the outer arm 162 radially outward.

It is to be appreciated that the control element 24 and the nut element 58, including the bushing 76 and the locking device 28, rotate together so that the locking device is not subject to any significant torsional twisting forces. This arrangement avoids interference with the rotational movement of the control element and enhances the useful life of the locking device 28. Therefore, the biasing means 168 urges both the outer arm 162 outward against the control element 24 and the inner arm 160 against the bushing 76 thereby locking the locking mechanism 28 against the bushing 76. One device usable as a locking mechanism 28 is part no. X27611 made by Bal Seal Engineering Company, Inc., Santa Ana, Calif.

Referring now to FIGS. 10, 11, and 12, an alternate embodiment of a locking device, generally indicated at 200, is described in detail. The locking device 200, in this embodiment, is usable in a manipulation handle 174 constructed in an alternate configuration to the previous handle 11, but having many elements in common. The alternative handle 174 likewise includes the handle body 32 rotatably mounting the cylindrical nut element 58 therein. The cylindrical nut element is likewise concentrically disposed over the tubular shaft 48 having an inner lumen 50 and the longitudinal slot 52 wherein the proximal end of the shaft is seated within the handle body 32.

The catheter body member 12 is mounted to a strain relief 176 constructed in a different configuration than the strain relief 90 described above. The strain relief is mounted at the distal end of the handle and has a smooth cylindrical portion 178 and a frustoconical converging forward portion 180. The cylindrical portion of the strain relief has an axial tubular shaft receiving bore 182 therein, the forward portion of the bore 182 converging frustoconically to a smaller diameter axial bore 184 extending to the distal tip of the strain relief. A pair of transversely aligned and opposing threaded set screw bores 186 are formed in the cylindrical portion of the bore. The shaft receiving bore 182 of the strain relief is disposed over the shaft 48 and a pair of respective set screws (not shown) are received in the set screw bores to securely anchor the strain relief 176 to the distal end of the tubular shaft 48.

In general, the locking device 200 comprises an annular forward ring 202, an annular middle ring 204, an annular spring 206, an annular rear ring 208, and a plurality of balls 210. The locking device 200 is mounted to a control element 188 constructed in a different configuration than the control element 24 described above, but having many elements in common with control element 24. Likewise, the control element 188 is slidably disposed over the nut element 58 and is longitudinally slidable relative to the shaft 48 and handle body 32 to control the shape of the distal end 16 of the catheter body member 12.

The control element 188 of the alternative handle configuration includes a forward control element 212 and a rear control element 214. The forward control element is generally cylindrical and has a smooth axial bore 215 therethrough sized for slidable receipt of the cylindrical portion of the strain relief 176. The rearward end of the forward control element is flared to a flange 216 having a plurality of forward axial screw bores 218 equiangularly spaced apart (FIG. 10). The rear control element is generally cylindrical having an axial bore therethrough including splines (not shown), similar to the splines 80 of the control element shown in FIG. 6, sized for longitudinal slidable receipt within longitudinal tracks (not shown) of the nut element 58. The forward end of the rear control element is flared to a flange 220 having a plurality of threaded rear axial screw bores 222 equiangularly spaced apart in complementary relationship with the forward axial screw bores 218 of the forward control element 212. The forward inner portion of the rear control element 214 is formed with an annular retention groove 224 for receipt of the locking device 200.

The forward ring 202 of the locking device 200 is essentially a flat washer having an inner diameter greater than that of the shaft 48 and an outer diameter less than the inner diameter of the control element bore 215. The forward ring includes a plurality of axial bores 226 formed through the ring, each bore equiangularly spaced apart from each other and each bore spaced the same radial distance from the central axis. A plurality of angularly tapered slots 228, in this instance three, are formed in a countersink-like orientation and at a diverging angle from the inner diameter of the forward surface of the ring rearwardly and outwardly to the rear surface of the forward ring. The width of the slots is selected to capture the plurality of balls 210 therein when assembled. The angle of the slots may be forty-five degrees relative to the central axis in a rearwardly diverging direction.

The middle ring 204 is substantially a flat washer formed with an inwardly projecting rectangular tang 230 having a width sized for slidable receipt within the longitudinal slot 52 of the shaft 48. The proximal end of deflection control line 20 is soldered, or connected by other means, to the forward surface of the tang 230 at generally the central axis of the middle ring. The inner diameter of the middle ring is slightly greater then the diameter of the shaft 48, and the outer diameter thereof is slightly less than the diameter of the retention groove 224 of the rear control element 214. The middle ring includes a plurality of axial bores 232 equiangularly spaced apart and at equal radial distances from the central axis, the middle ring bores located in complementary relationship to the axial bores 226 of the forward ring 202. The forward and middle ring bores are of substantially the same diameter and are of the same number and location.

The rear ring 208 is substantially a flat washer having an inner diameter greater than the shaft 48 and an outer diameter substantially the same as the outer diameter of the middle ring 204. The rear ring includes a plurality of threaded axial bores 234 equiangularly spaced apart and spaced the same radial distance from the central axis. The rear ring's threaded bores are located in complementary relationship to the forward and middle ring bores, 226 and 232, and are of the same number.

The annular spring 206 is generally in the form of a ring-like wavy washer in this embodiment, however a large diameter annular coil spring may be usable. The wavy washer spring has an inner diameter substantially the same diameter as the control element bore 215 and an outer diameter substantially the same diameter as the outer diameter of the middle ring 204. Additionally, other biasing means may be used in place of the wavy washer. For example, a plurality of equally spaced compressed coil springs may be used.

When assembled, the wavy washer spring 206 is disposed between the middle and rear rings 204 and 208, and the respective rings and spring 206 are disposed over the tubular shaft 48 so that the tang 230 of the middle ring is slidably received within the longitudinal slot 52 of the shaft 48. The rear and middle rings are received within the annular retention groove 224 of the rear control element 214. The forward ring 202 is disposed over the shaft so that the tapered slots 228 are in confronting relationship with the middle ring and a respective ball 210 is disposed within each of the slots between middle ring and the shaft.

A plurality of threaded screws 236 are received through the respective plurality of forward and middle ring bores, 226 and 232, and threaded within the respective rear ring bores 234. As the screws 236 are tightened, the balls 210 press against the middle ring 204 and the shaft 48 to compress the wavy washer spring 206 between the rear and middle rings. The tapered slots 228 of the forward ring 202 redirect the axial force of the spring 206 through the balls to press the balls radially against the shaft 48. The surfaces of the balls exert a radial inward force pressing against the shaft 34 imparting a continuous contact force thereto.

The forward control element 212 is then engaged to the rear control element 214, by means of control element screws 238 (FIG. 10) to capture the rear and middle rings 204 and 208 of the locking device 200 within the retention groove 224 between the rear and forward control elements. The tang 230 of the middle ring 204 is received within the longitudinal slot 52 of the shaft 48 so that rotation of the rings 202, 204, and 208 is constrained, while longitudinal movement of the rings and control element relative to the shaft 48 and handle body 32 is provided. In one embodiment, the material used to construct the rings was stainless steel.

Referring again to FIG. 10, longitudinal sliding movement of the control element 188 affects the distal end curvature of the body member 12. Movement of the control element in the proximal axial direction relative to the handle body 32 moves the locking device 200, the tang 230 of the middle ring 204, and the control line 20 to create tension on the control line to deflect the distal end 16 of the catheter body member 12. The physician may selectively position and reposition the control element 188 longitudinally to achieve a desired deflection of the catheter body member distal end.

The wavy washer spring 206 is selected to provide an axial biasing force sufficient to hold the control element 188 in a selected position, overcoming the longitudinal force applied by the deflected distal end tending to straighten itself. The locking device 200 overcomes the straightening or restoring force of the body member 12 incurred when the control element 188 is moved to any selected position over its entire longitudinal range of motion. The locking device 200 is also designed not to exert an inordinate amount of contact force against the shaft, so that the physician without undue effort, can slide the element 188 to various selected positions. The tendency of the balls 210 to stay where they are and continuously apply the radial force against the shaft 48 is overcome by the gap 205 in the retention groove 224. That is, the groove 224 is larger than the combination of the three rings 204, 206, and 208. As the control element is moved longitudinally and a wall of the groove 224 comes into contact with one outer ring or the other 204 and 208, depending on the sliding direction, that contact will relieve some of the axial force on the ball causing it to apply less radial pressure against the shaft 48. Thus, the rings 204, 206, and 208 "float" in the groove 224 having the beneficial effect just discussed.

In both foregoing locking mechanism embodiments, the physician may release the control element 24 or 188 once the distal end deflection of the body member 12 has been obtained and that deflection will be preserved.

In both handle configurations, the stiffening member 30 is passed proximally through the distal end bore of the strain relief 90 or 176 and is secured at its proximal end to the inward projection 84 on the screw element 82 of the handle body 32 by suitable means such as by brazing, soldering or by an adhesive.

Referring now to FIGS. 4 and 10, rotation of the control element 24 or 188 relative to the handle body 32, rotates the nut element 58, which in turn moves the screw element 82 longitudinally along the tubular shaft 48. Because the stiffening member 30 is connected to the inward projection 84 on the screw element 82, longitudinal movement of the screw element results in longitudinal movement of the stiffening member 30 within the catheter body member 12. The stiffening member 30 has sufficient column strength to communicate the thrust applied to the proximal end to the distal end thereof and otherwise stiffen the distal end 16 of the catheter body member 12 and control distal end curvature as shown in FIGS. 2 and 3.

In the alternate locking mechanism shown in FIGS. 10 through 12, the control element 188 rotates relative to the locking device 200 because the tang 230 of the middle ring 204 is rotatably constrained within the longitudinal slot 52 of the tubular shaft 48. However, the control element can rotate around the middle and rear rings 204 and 208 of the locking device 200 due to their mounting within the annular retaining groove 224 of the control element 188. Thus the locking mechanism 200 provides against interference with the rotation of the control element so that ease in operating the stiffening member 30 is not compromised.

From the foregoing, it can be appreciated that the invention provides a locking mechanism for use in a steerable catheter 10 that has the ability to lock the distal end curvature of the catheter at the selected positions. Furthermore, the locking device minimally influences the operating characteristics of the stiffening member control device. The locking mechanism is easy to operate, relatively inexpensive to manufacture, and reliable in use.

While the invention has been described herein in terms of certain embodiments, it may become apparent to one skilled in the art that the invention is susceptible to modifications and adaptations without the exercise of inventive faculty. Thus, it should be understood that various changes in form, detail and usage of the present invention may be made without departing from the spirit and scope of the invention.

What is claimed is:

1. A catheter having a deflectable distal tip, the catheter comprising:
    a resilient body member having a distal end and a proximal end, the body member having a resilient force tending to maintain and restore the distal end of the body member in a predetermined shape;
    a manipulation handle attached to the proximal end of the body member having first and second elements slidably movable in longitudinal relation to each other;
    a deflection control device mounted in the body member and connected at a proximal end to the first element of the handle and extending into the distal end of the body member wherein said sliding longitudinal movement of the first element in relation to the second element results in movement of the control device in the distal end, said movement of the control device in one direction causing deflection of the distal end from its predetermined shape against the restoring force, said restoring force also tending to cause sliding movement of the first element in relation to the second element;
    a locking device having a contact member and a biasing member mounted on the first element with the contact member being continuously urged into contact with the second element by the biasing member, said biasing member comprising at least a partially compressed resilient member providing a force against said contact member that exceeds and directly opposes the restoring force provided by the body member so that the locking member holds the first and second elements in a selected position relative to one another and thereby maintains the control device at a selected position in the distal end.

2. A catheter having a deflectable distal tip, the catheter comprising:
    a resilient body member having a distal end and a proximal end, the body member having a resilient force tending to maintain and restore the distal end of the body member in a predetermined shape;
    a manipulation handle attached to the proximal end of the body member having first and second elements slidably movable in longitudinal relation to each other;
    a deflection control device mounted in the body member and connected at a proximal end to the first element of the handle and extending into the distal end of the body member wherein said longitudinal sliding movement of the first element in relation to the second element results in movement of the control device in the distal end, said movement of the control device in one direction causing deflection of the distal end from its predetermined shape against the restoring force, said restoring force also tending to cause sliding movement of the first element in relation to the second element;
    a locking device having a contact member and a biasing member mounted on the first element with the contact member being continuously urged into contact with the second element by the biasing member, said biasing member providing a force against said contact member that exceeds and directly opposes the restoring force provided by the body member so that the locking member holds the first and second elements in a selected position relative to one another and thereby maintains the control device at a selected position in the distal end;
    wherein the contact member comprises an annular contact arm having a circumferential contact surface; and
    wherein the biasing member is a resilient member that is at least partially compressed into contact with the contact arm to urge the arm against the second element and bias the contact surface to exert radial pressure against the second element.

3. A catheter having a deflectable distal tip, the catheter comprising:
    a resilient body member having a distal end and a proximal end, the body member having a resilient force tending to maintain and restore the distal end of the body member in a predetermined shape;
    a manipulation handle attached to the proximal end of the body member having first and second elements movable in relation to each other;
    a deflection control device mounted in the body member and connected at a proximal end to the first element of the handle and extending into the distal end of the body member wherein said movement of the first element in relation to the second element results in movement of the control device in the distal end, said movement in one direction causing deflection of the distal end from its predetermined shape against the restoring force, said restoring force also tending to cause movement of the first element in relation to the second element;
    a locking device having a contact member and a biasing member mounted on the first element with the contact member being continuously urged into contact with the second element by the biasing member, said biasing member providing a force against said contact member that exceeds the restoring force provided by the body member so that the locking member holds the first and second elements in a selected position relative to one another and thereby maintains the control device at a selected position in the distal end, wherein the contact member comprises an annular contact arm having a circumferential contact surface, the biasing member being disposed in contact with the contact arm to urge the contact arm against the second element and bias the contact surface to exert radial pressure against the second element, the contact member being U-shaped in cross section having inner and outer arms, one of the arms being the contact arm and the volume between the arms defining an annulus in which the biasing member is disposed, the biasing member having a size selected to urge the contact arm outward from the annulus into contact with the second element.

4. The catheter of claim 3 wherein the biasing member comprises an annular spring of a size selected so that energy is stored in the spring when mounted in the annulus tending to urge the contact surface into contact with the other element.

5. The catheter of claim 4 wherein the spring comprises a slanted coil spring under radial compression when disposed in the annulus of the contact member, the spring tending to expand and displace the contact arm into contact with the other element pressing the contact surface against the other element.

6. A catheter having a deflectable distal tip, the catheter comprising:

a resilient body member having a distal end and a proximal end, the body member having a resilient force tending to maintain and restore the distal end of the body member in a predetermined shape;

a manipulation handle attached to the proximal end of the body member having first and second elements movable in relation to each other, wherein the second element surrounds the first element and slides in relation to the first element;

a deflection control device mounted in the body member and connected at a proximal end to the first element of the handle and extending into the distal end of the body member wherein said sliding movement of the first element in relation to the second element results in movement of the control device in the distal end, said movement in one direction causing deflection of the distal end from its predetermined shape against the restoring force, said restoring force also tending to cause movement of the first element in relation to the second element;

a locking device having a contact member and a biasing member mounted on the first element with the contact member being continuously urged into contact with the second element by the biasing member, said biasing member providing a force against said contact member that exceeds and directly opposes the restoring force provided by the body member so that the locking member holds the first and second elements in a selected position relative to one another and thereby maintains the control device at a selected position in the distal end, wherein the contact member is mounted at a fixed position on the first member and is biased into contact with the second member to secure the second member at a selected position to which it has been slid in relation to the first member.

7. The catheter of claim 6 wherein:

the first and second members are mounted in a manipulation handle which is attached to the proximal end of the body member of the catheter; and
the second member is mounted at an external position on the manipulation handle so that it is available for slidable movement by the application of external force by a catheter operator.

8. A catheter having a deflectable distal tip, the catheter comprising:

a resilient body member having a distal end and a proximal end, the body member having a resilient force tending to maintain and restore the distal end of the body member in a predetermined shape;

a manipulation handle attached to the proximal end of the body member having first and second elements movable in relation to each other, the first element and second element mounted so as to be movable axially and rotationally relative to one another;

a deflection control device mounted in the body member and connected at a proximal end to the first element of the handle and extending into the distal end of the body member wherein said axial and rotational movement of the first element in relation to the second element results in movement of the control device in the distal end, said movement in one direction causing deflection of the distal end from its predetermined shape against the restoring force, said restoring force also tending to cause movement of the first element in relation to the second element;

a locking device having a contact member and a biasing member mounted on the first element with the contact member being continuously urged into contact with the second element by the biasing member, the contact member comprising a lubricous material that contacts the second element, said biasing member providing a force against said contact member that exceeds and directly opposes the restoring force provided by the body member so that the locking member holds the first and second elements in a selected position relative to one another and thereby maintains the control device at a selected position in the distal end, said locking device mounted so that it provides no significant force to oppose the rotation.

9. A catheter having a deflectable distal tip, the catheter comprising:

a resilient body member having a distal end and a proximal end, the body member having a resilient force tending to maintain and restore the distal end of the body member in a predetermined shape;

a manipulation handle attached to the proximal end of the body member having first and second elements movable in relation to each other, the first element and second element mounted so as to be movable axially and rotationally relative to one another;

a deflection control device mounted in the body member and connected at a proximal end to the first element of the handle and extending into the distal end of the body member wherein said axial and rotational movement of the first element in relation to the second element results in movement of the control device in the distal end, said movement in one direction causing deflection of the distal end from its predetermined shape against the restoring force, said restoring force also tending to cause movement of the first element relation to the second element;

a locking device having a contact member and a biasing member mounted on the first element with the contact member being continuously urged into contact with the second element by the biasing member, the contact member comprising at least a partially compressed resilient member comprising a lubricous material that contacts the second element, said biasing member providing a force against said contact member that exceeds the restoring force provided by the body member so that the locking member holds the first and second elements in a selected position relative to one another and thereby maintains the control device at a selected position in the distal end, said locking device mounted so that it provides no significant force to oppose the rotation, wherein the first element includes an annular groove in which the contact member is mounted.

10. A catheter having a deflectable distal tip, the catheter comprising:

a resilient body member having a distal end and a proximal end, the body member having a resilient restoring force tending to maintain and restore the distal end of the body member in a predetermined shape;

a manipulation handle attached to the proximal end of the body member having first and second elements movable in relation to each other;

a deflection control device mounted in the body member and connected at a proximal end to the first element of the handle and extending into the distal end of the body member wherein said movement of the first element in relation to the second element results in movement of the control device in the distal end, said movement in one direction causing deflection of the distal end from its predetermined shape against the restoring force, said restoring force also tending to cause movement of the first element in relation to the second element;

a locking device having a contact member and a biasing member mounted on the first element with the contact member being continuously urged into contact with the second element by the biasing member, the contact member comprising a ball, said biasing member providing a biasing force against said contact member that exceeds the restoring force provided by the body member so that the locking member holds the first and second elements in a selected position relative to one another and thereby maintains the control device at a selected position in the distal end, wherein the biasing member urges the ball into contact with the second element to apply locking force to the second element to hold it in the selected position.

11. The catheter of claim 10 wherein:

the biasing member provides an axial force against the ball;

a mounting ring is disposed opposite the biasing member from the ball and constrains the movement of the ball in a radial direction in relation to the second element so that the biasing force applied to the ball is redirected to the radial direction against the second element.

12. The catheter of claim 11 wherein the mounting ring includes a biasing surface formed at a forty-five degree angle relative to the axial biasing force against the ball to redirect the force applied to the ball in the radial inward direction against the second element.

13. The catheter of claim 12 wherein:

the biasing surface comprises three tapered slots and a respective ball is disposed in each of the respective slots whereby the biasing member provides the axial force against each of the respective balls and the tapered slots redirect the force applied to the balls in the radial direction against the second element.

14. The catheter of claim 13 wherein the three tapered slots are at forty-five degree angles relative to the axial force to redirect the axial force applied to the balls in the radial direction against the other element.

15. The catheter of claim 13 wherein:

the biasing member comprises an annular metallic wavy washer spring mounted so that it is under axial compression to provide the axial biasing force;

the spring forces the balls into contact with the tapered slots redirecting the axial force of the spring radially.

16. The catheter of claim 10 wherein the biasing member comprises an annular metallic wavy washer spring mounted so that it is under axial compression to provide the axial biasing force.

17. A catheter having a deflectable distal tip, the catheter comprising:

a resilient body member having a distal end and a proximal end, the body member having a force tending to maintain and restore the distal end of the body member in a predetermined shape;

a manipulation handle attached to the proximal end of the body member having first and second elements slidably moveable in longitudinal relation to each other;

a deflection control device mounted in the body member and connected at a proximal end to the first element of the handle and extending into the distal end of the body member wherein said sliding longitudinal movement of the first element in relation to the second element results in movement of the deflection control device in the distal end, said movement in one direction causing variation in the deflection of the distal end from its predetermined shape against the restoring force, said restoring force also tending to cause movement of the first element in relation to the second element;

a locking device contained entirely within the manipulation handle, and being inaccessible to a user, that holds the first and second elements in a selected position relative to one another and thereby maintains the control device at a selected position in the distal end, wherein the locking device comprises:

a contact member that comprises an annular contact arm having a circumferential contact surface; and a biasing member comprising a resilient member at least partially compressed into contact with the contact arm to urge the contact arm against the second element and bias the contact surface to exert radial pressure against the second element.

18. The catheter of claim 17 wherein:

the contact member is U-shaped in cross section having inner and outer arms, one of the arms being the contact arm and the volume between the arms defining an annulus in which the biasing member is disposed, the biasing member having a size selected to urge the contact arm outward from the annulus into contact with the second element.

19. The catheter of claim 17 wherein:

the second element surrounds the first element and slides in relation to the first element;

the contact member is mounted at a fixed position on the first element and is biased into contact with the second element to secure the second element at a selected position to which it has been slid in relation to the first element.

20. The catheter of claim 19 wherein:

the first and second elements are mounted in a manipulation handle which is attached to the proximal end of the body member of the catheter; and the second element is mounted at an external position on the manipulation handle so that it is available for slidable movement by the application of external force by a catheter operator.

21. The catheter of claim 17 wherein:

the first element and second element are mounted so as to be movable axially and rotationally relative to one another;

the contact member comprises a lubricous material that contacts the second element and is mounted so that the contact member provides no significant force to oppose the rotation.

22. The catheter of claim 21 wherein the first element includes an annular groove in which the contact member is mounted.

23. The catheter of claim 17 wherein the locking device is self-adjusting and the biasing member provides a continuous force against the contact member.

* * * * *